United States Patent
Ebert et al.

(10) Patent No.: US 10,414,856 B2
(45) Date of Patent: *Sep. 17, 2019

(54) POLYETHERAMINES BASED ON 1,3-DIALCOHOLS

(71) Applicant: BASF SE, Ludwigshafen (DE)

(72) Inventors: Sophia Ebert, Mannheim (DE); Bjoern Ludolph, Ludwigshafen (DE); Christian Eidamshaus, Mannheim (DE); Stefano Scialla, Rome (IT); Kevin Christmas, Mason, OH (US); Amy Eichstadt Waun, West Chester, OH (US); Brian J. Loughnane, Sharonville, OH (US); Darren Rees, Newcastle (GB); Frank Huelskoetter, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 54 days.

This patent is subject to a terminal disclaimer.

(21) Appl. No.: 15/513,637

(22) PCT Filed: Sep. 10, 2015

(86) PCT No.: PCT/EP2015/070727
§ 371 (c)(1),
(2) Date: Mar. 23, 2017

(87) PCT Pub. No.: WO2016/045983
PCT Pub. Date: Mar. 31, 2016

(65) Prior Publication Data
US 2017/0298174 A1    Oct. 19, 2017

Related U.S. Application Data

(60) Provisional application No. 62/055,016, filed on Sep. 25, 2014.

(51) Int. Cl.
*C11D 1/00* (2006.01)
*C11D 3/26* (2006.01)
(Continued)

(52) U.S. Cl.
CPC .............. *C08G 59/50* (2013.01); *A61K 8/86* (2013.01); *A61Q 5/02* (2013.01); *A61Q 19/10* (2013.01);
(Continued)

(58) Field of Classification Search
CPC .......... C11D 3/30; C11D 3/3723; B29C 33/56; B29C 35/00
(Continued)

(56) References Cited

U.S. PATENT DOCUMENTS 5,912,189 A    6/1999  Wolak et al.
9,193,939 B2 * 11/2015  Hulskotter ........... C11D 3/0036
(Continued)

FOREIGN PATENT DOCUMENTS

EP    0433777 A2    6/1991
EP    0636409 A1    2/1995
(Continued)

OTHER PUBLICATIONS

Beuth, "Determination of Hydroxyl Value", DIN 53240, 1971. (Translation 2007).
(Continued)

*Primary Examiner* — Gregory R DelCotto
(74) *Attorney, Agent, or Firm* — Armstrong Teasdale LLP

(57) ABSTRACT

This invention relates to polyetheramines based on 1,3-dialcohols, in particular to an etheramine mixture comprising at least 90% by weight, based on the total weight of the etheramine mixture, of an amine of Formula (I) and/or (II), Formula (I)
$$Z_1-A_1\!\!\left[\!\!-\!\!O-A_2\!\right]_{(y_1-1)}\!\!\left[\!\!-\!\!O\!\!\underset{R_2}{\underset{|}{\overset{R_1}{\underset{|}{C}}}}\!\!-\!\!A_3\!\right]_{(y-1)}\!\!-\!\!O\!\!\underset{R_3}{\underset{|}{\overset{R_6}{\underset{|}{C}}}}\!\!\underset{R_4}{\underset{|}{\overset{R_5}{\underset{|}{C}}}}\!\!-\!\!A_4\!\!-\!\!O\!\!\left[\!\!-\!\!A_5\!\!-\!\!O\!\right]_{(x-1)}\!\!-\!\!A_6\!\!-\!\!Z_2$$

Formula (II)
$$Z_3\!\!-\!\!\underset{R_8}{\underset{|}{\overset{R_7}{\underset{|}{C}}}}\!\!\underset{R_{10}}{\underset{|}{\overset{R_{12}}{\underset{|}{C}}}}\!\!\underset{R_{11}}{\underset{|}{\overset{R_{12}}{\underset{|}{C}}}}\!\!-\!\!A_7\!\!-\!\!O\!\!\left[\!\!-\!\!A_8\!\!-\!\!O\!\right]_{(x-1)+(y-1)+1}\!\!-\!\!A_9\!\!-\!\!Z_4$$

wherein $R_1$-$R_{12}$ are independently selected from H, alkyl, cycloalkyl, aryl, alkylaryl, or arylalkyl, wherein at least one of $R_1$-$R_6$ and at least one of $R_7$-$R_{12}$ is different from H, wherein $A_1$-$A_9$ are independently selected from linear or branched alkylenes having 2 to 18 carbon atoms, wherein $Z_1$-$Z_4$ are independently selected OH, $CH_2CH_2CH_2NH_2$, $NH_2$, NHR' or NR'R", wherein the degree of amination is <50%, wherein R' and R" are independently selected from alkylenes having 2-6 carbon atoms, and wherein the sum of x+y is in the range of from 2 to 200, wherein x≥1 and y≥1; and $x_1+y_1$ is in the range of from 2 to 200.

24 Claims, No Drawings

(51) Int. Cl.
*C11D 3/37* (2006.01)
*C08G 59/50* (2006.01)
*B29C 33/56* (2006.01)
*B29C 35/00* (2006.01)
*C11D 3/30* (2006.01)
*C07C 213/02* (2006.01)
*C08G 65/26* (2006.01)
*C11D 1/44* (2006.01)
*C09J 177/06* (2006.01)
*C08G 18/50* (2006.01)
*C08G 18/38* (2006.01)
*C08G 65/325* (2006.01)
*C08G 65/333* (2006.01)
*C08G 69/40* (2006.01)
*A61K 8/86* (2006.01)
*A61Q 5/02* (2006.01)
*A61Q 19/10* (2006.01)
*C09J 163/00* (2006.01)
*C09J 177/00* (2006.01)
*C11D 3/22* (2006.01)
*C09J 175/02* (2006.01)
*C09J 175/04* (2006.01)
*C08L 73/00* (2006.01)

(52) U.S. Cl.
CPC ............. *B29C 33/56* (2013.01); *B29C 35/00* (2013.01); *C07C 213/02* (2013.01); *C08G 18/3819* (2013.01); *C08G 18/5024* (2013.01); *C08G 59/504* (2013.01); *C08G 65/26* (2013.01); *C08G 65/2609* (2013.01); *C08G 65/3255* (2013.01); *C08G 65/33365* (2013.01); *C08G 69/40* (2013.01); *C08L 73/00* (2013.01); *C09J 163/00* (2013.01); *C09J 175/02* (2013.01); *C09J 175/04* (2013.01); *C09J 177/00* (2013.01); *C09J 177/06* (2013.01); *C11D 1/44* (2013.01); *C11D 3/225* (2013.01); *C11D 3/30* (2013.01); *C11D 3/3707* (2013.01); *C11D 3/3723* (2013.01); *C08G 2650/50* (2013.01)

(58) Field of Classification Search
USPC .... 510/475, 499, 505, 506; 106/38.2, 38.22, 106/287.23
See application file for complete search history.

(56) References Cited

U.S. PATENT DOCUMENTS

| | | | | |
|---|---|---|---|---|
| 9,487,739 | B2* | 11/2016 | Loughnane | C11D 3/38636 |
| 9,540,592 | B2* | 1/2017 | Hulskotter | C11D 3/0036 |
| 9,617,502 | B2* | 4/2017 | Loughnane | C11D 3/3761 |
| 9,631,163 | B2* | 4/2017 | Hulskotter | C11D 3/3707 |
| 9,637,710 | B2* | 5/2017 | Hulskotter | C11D 3/3707 |
| 10,190,078 | B2* | 1/2019 | Hulskotter | C11D 3/386 |
| 2014/0296124 | A1* | 10/2014 | Hulskotter | C11D 3/0036 510/300 |
| 2014/0296127 | A1* | 10/2014 | Hulskotter | C11D 3/0036 510/392 |
| 2015/0275142 | A1* | 10/2015 | Hulskotter | C11D 3/3723 510/320 |
| 2015/0275143 | A1* | 10/2015 | Hulskotter | C11D 3/3723 510/320 |
| 2015/0315523 | A1* | 11/2015 | Hulskotter | C11D 3/386 510/226 |
| 2015/0315524 | A1* | 11/2015 | Hulskotter | C11D 3/3707 510/235 |
| 2016/0075970 | A1* | 3/2016 | Hulskotter | C11D 3/0036 510/300 |
| 2016/0075975 | A1* | 3/2016 | Loughnane | C11D 3/3761 510/320 |
| 2017/0121642 | A1* | 5/2017 | Loughnane | C11D 3/38636 |

FOREIGN PATENT DOCUMENTS

| | | | |
|---|---|---|---|
| EP | 0696572 A1 | 2/1996 | |
| EP | 0742045 A1 | 11/1996 | |
| EP | 0963975 A1 | 12/1999 | |
| WO | 8607603 A1 | 12/1986 | |
| WO | 9003423 A1 | 4/1990 | |
| WO | WO-9502681 A1 | 1/1995 | |
| WO | WO-0063334 A1 * | 10/2000 | ............... C11D 1/83 |
| WO | 0176729 A2 | 10/2001 | |
| WO | 2009065738 A2 | 5/2009 | |
| WO | 2009138387 A1 | 11/2009 | |
| WO | 2009153193 A1 | 12/2009 | |
| WO | 2010010075 A1 | 1/2010 | |
| WO | 2010026030 A1 | 3/2010 | |
| WO | 2010026066 A1 | 3/2010 | |
| WO | 2011067199 A1 | 6/2011 | |
| WO | 2011067200 A1 | 6/2011 | |
| WO | 2011087793 A1 | 7/2011 | |
| WO | WO-2013/072289 A1 | 5/2013 | |
| WO | 2014154783 A1 | 10/2014 | |
| WO | 2015169373 A1 | 11/2015 | |

OTHER PUBLICATIONS

Extended European Search Report for EP Application No. 14186427.2, dated Mar. 9, 2015, 10 pages.
International Preliminary Report on Patentability for PCT Patent Application No. PCT/EP2015/070727, dated Apr. 6, 2017, 14 pages.
International Search Report issued in International Patent Application No. PCT/EP2015/070727 dated Jan. 5, 2015.
Written Opinion issued in International Patent Application No. PCT/EP2015/070727 dated Mar. 31, 2016.
Anonymous: "Technical Bulletin,Jeffamine Polyetheramines", Jan. 1, 2012 (Jan. 1, 2012), pp. 1-8, XP055235794, Retrieved from the Internet http://www.huntsman.com/performance_products/Media Library/a_MC348531CFA3EA9A2E040EBCD2B6B7B06/Products_MC348531D0B9FA9A2E040EBCD2B6B7B06/Amines_MC348531D0BECA9A2E040EBCD2B6B7B06/Polyetheramines JE_MC348531D0E07A9A2E040EBCD2B6B7B06/files/Jeffamine Polyetheramines booklet - 10-12R1_2.pdf.

* cited by examiner

POLYETHERAMINES BASED ON 1,3-DIALCOHOLS

CROSS-REFERENCE TO RELATED APPLICATIONS

This application is a U.S. National Phase Application of PCT/EP2015/070727, filed Sep. 10, 2015, which claims the benefit of priority to EP Application No. 14186427.2, filed Sep. 25, 2014, and to U.S. Application No. 62/055,016, filed Sep. 25, 2014, the contents of which are hereby expressly incorporated by reference in their entirety.

COMMON OWNERSHIP UNDER JOINT RESEARCH AGREEMENT 35 U.S.C. 102(C)

The subject matter disclosed in this Application was developed, and the claimed invention was made by, or on behalf of, one or more parties to a Joint Research Agreement that was in effect on or before the effective filing date of the claimed invention. The parties to the Joint Research Agreement are as follows: BASF SE and The Procter and Gamble Company.

This invention relates to polyetheramines based on 1,3-dialcohols, in particular to polyetheramine mixtures obtainable by the alkoxylation and amination or reductive ethoxylation of 1,3-dialcohols.

Due to the increasing popularity of easy-care fabrics made of synthetic fibers as well as the ever increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing result at such low temperatures, results comparable to those obtained with hot water washes, the demands on low-temperature detergents are especially high.

It is known to include certain additives in detergent compositions to enhance the detergent power of conventional surfactants so as to improve the removal of grease stains at temperatures of 60° C. and below.

WO 86/07603 discloses that detergent composition comprising an aliphatic amine compound, in addition to at least one synthetic anionic and/or nonionic surfactant, are known and have led to improved cleaning results even at low wash temperatures. These compounds are said to contribute to the improvement of the washing performance of the detergent at lower temperatures.

Also, the use of linear, alkyl-modified (secondary) alkoxypropylamines in laundry detergents to improve cleaning at low temperatures is known (WO90/03423). These known laundry detergents, however, are unable to achieve satisfactory cleaning when laundry is washed at cold temperatures.

Furthermore, the use of linear, primary polyoxyalkyleneamines (e.g., Jeffamine® D-230) to stabilize fragrances in laundry detergents and provide longer lasting scent is also known (WO2009/065738). Also, the use of high-molecular-weight (molecular weight of at least about 1000), branched, trifunctional, primary amines (e.g., Jeffamine® T-5000 polyetheramine) to suppress suds in liquid detergents is known (WO01/76729).

Additionally, WO 2011/087793 reads on etheramine mixtures comprising at least 10 wt % of an alkoxylated monoether amine based on polyhydric alcohols containing 2 to 4 hydroxyl groups as the starting compound. A process for the manufacture of these etheramine mixtures is also disclosed. These products find an application as a curing agent or as a raw material in the synthesis of polymers.

There is a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for improved amine compositions which provide improved grease removal from fabrics and other soiled materials and at the same time do not negatively impact the clay cleaning.

It was an object of the present invention to provide compounds which would improve the washing performance of detergents at low temperatures, i.e. at temperatures as low as 30° C. or even lower.

This goal was achieved with an etheramine mixture comprising at least 90% by weight, based on the total weight of the etheramine mixture, of an amine of Formula (I) and/or (II),

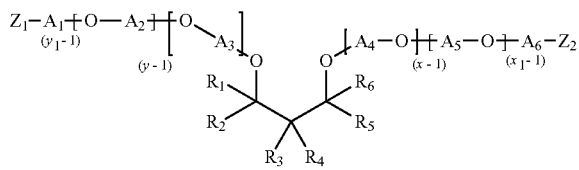

Formula (I)

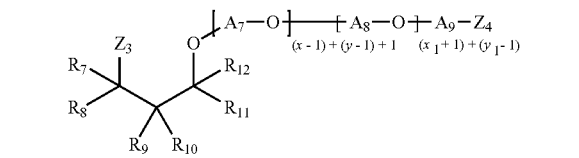

Formula (II)

wherein $R_1$-$R_{12}$ are independently selected from H, alkyl, cycloalkyl, aryl, alkylaryl, or arylalkyl,
wherein at least one of $R_1$-$R_6$ and at least one of $R_7$-$R_{12}$ is different from H, wherein $A_1$-$A_9$ are independently selected from linear or branched alkylenes having 2 to 18 carbon atoms, preferably 2-10 carbon atoms, most preferably 2-5 carbon atoms, wherein $Z_1$-$Z_4$ are independently selected from OH or $CH_2CH_2CH_2NH_2$, $NH_2$, NHR' or NR'R", wherein the degree of amination is <50%, wherein R' and R" are independently selected from alkylenes having 2 to 6 carbon atoms, and wherein the sum of x+y is in the range of about 2 to about 200, wherein x≥1 and y≥1; and $x_1$+$y_1$ is in the range of about 2 to about 200, preferably 2-20, most preferably 2-10, wherein $x_1$≥1 and $y_1$≥1.

Preferably, the sum of x and y is in the range of 2 to 20, more preferably in the range of 2 to 10, even more preferably in the range of 3 to 8 and even more preferably in the range of 4 to 6.

Preferably, the sum of $x_1$ and $y_1$ is in the range of 2 to 20, more preferably in the range of 2 to 10, even more preferably in the range of 3 to 8 and even more preferably in the range of 2 to 4.

In a preferred embodiment, the etheramine mixture comprises at least 95% by weight, based on the total weight of the etheramine mixture, of the amine of Formula (I) and/or (II).

In another preferred embodiment, $A_1$-$A_9$ are independently selected from the group consisting of ethylene, propylene, or butylene, preferably each of $A_1$-$A_9$ is propylene.

In Formula (I) or (II), $R_1$, $R_2$, $R_5$, $R_6$, $R_7$, $R_8$, $R_{11}$, and $R_{12}$ are H and $R_3$, $R_4$, $R_9$, and $R_{10}$ are independently selected from C1-16 alkyl or aryl.

Preferably, in Formula (I) or (II), $R_1$, $R_2$, $R_5$, $R_6$, $R_7$, $R_8$, $R_{11}$, and $R_{12}$ are H and $R_3$, $R_4$, $R_9$, and $R_{10}$ are independently selected from a butyl group, an ethyl group, a methyl group, a propyl group, or a phenyl group.

Even more preferably, in Formula (I) or (II), R3 and R9 are each an ethyl group, $R_1$, $R_2$, $R_5$, $R_6$, $R_7$, $R_8$, $R_{11}$, and $R_{12}$ are each H, $R_4$ and $R_{10}$ are each a butyl group.

The polyetheramine of Formula (I) or Formula (II) has a weight average molecular weight of about 290 to about 1000 grams/mole, preferably, of about 300 to about 700 grams/mole, even more preferably of about 300 to about 450 grams/mole.

The etheramine mixture comprising at least 90% by weight, based on the total weight of the etheramine mixture, of an etheramin of Formula (I) and/or (II) is obtainable by a process comprising the following steps:
 a) the reaction of 1,3-diols of Formula (III) with $C_2$-$C_{18}$ alkylene oxides, wherein the molar ratio of 1,3-diol to $C_2$-$C_{18}$ alkylene oxides is in the range of 1:2 to 1:10,

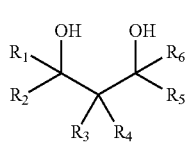

Formula (III)

with $R_1$-$R_6$ are independently of one another H, alkyl, cycloalkyl, aryl, alkylaryl, arylalkyl and at least one group selected from $R_1$-$R_6$ is different from H, followed by either
 b1) the amination of the alkoxylated 1, 3-diols with ammonia, or
 b2) reductive cyanoethylation of the alkoxylated 1, 3-diols.

In a preferred embodiment, this etheramine mixture comprising at least 95% by weight, based on the total weight of the etheramine mixture, of the obtained etheramine.

In a preferred embodiment the molar ratio of 1,3-diol to $C_2$-$C_{18}$ alkylene oxides is in the range of 1:3 to 1:8, even more preferably in the range of 1:4 to 1:6.

Preferably the $C_2$-$C_{18}$ alkylene oxides are selected from the group consisting of ethylene oxide, propylene oxide, butylene oxide or a mixture thereof, even more preferably $C_2$-$C_{18}$ alkylene oxide is propylene oxide.

Preferably in the 1,3-diol of Formula (III) $R_1$, $R_2$, $R_5$, $R_6$ are H and $R_3$, $R_4$ are C1-16 alkyl or aryl.

The 1,3-diol of Formula (III) is preferably selected from the group consisting of 2-butyl-2-ethyl-1,3-propanediol, 2-methyl-2-propyl-1,3-propanediol, 2-methyl-2-phenyl-1,3-propanediol, 2,2-dimethyl-1,3-propandiol, 2-ethyl-1,3-hexandiol.

Step a): Alkoxylation

Substituted 1,3 diols (Formula III) are synthesized according WO10026030, WO10026066, WO09138387, WO09153193, WO10010075.

Suitable 1,3-diols (Formula III) are for example: 2,2-dimethyl-1,3-propane diol, 2-butyl-2-ethyl-1,3-propane diol, 2-pentyl-2-propyl-1,3-propane diol, 2-(2-methyl)butyl-2-propyl-1,3-propane diol, 2,2,4-trimethyl-1,3-propane diol, 2,2-diethyl-1,3-propane diol, 2-methyl-2-propyl-1,3-propane diol, 2-ethyl-1,3-hexane diol, 2-phenyl-2-methyl-1,3-propane diol, 2-methyl-1,3-propane diol, 2-ethyl-2-methyl-1,3 propane diol, 2,2-dibutyl-1,3-propane diol, 2,2-di(2-methylpropyl)-1,3-propane diol, 2-isopropyl-2-methyl-1,3-propane diol, etc.

Preferred 1,3-diols are 2-butyl-2-ethyl-1,3-propanediol, 2-methyl-2-propyl-1,3-propanediol, 2-methyl-2-phenyl-1,3-propanediol.

Alkoxylated 1,3-diols are obtained by reaction of 1,3-diols (Formula III) with alkylene oxides and can be affected according to general alkoxylation procedures known in the art.

The alkoxylated 1,3-diols may be prepared in a known manner by reaction of 1,3-diols with alkylene oxides. Suitable alkylene oxides are $C_2$-$C_{18}$ alkylene oxides like ethylene oxide, propylene oxide, butylene oxide, pentene oxide, hexene oxide, decene oxide, dodecene oxide etc.

Preferred $C_2$-$C_{18}$ alkylene oxides are ethylene oxide, propylene oxide, butylene oxide or a mixture thereof.

The 1,3-diols are reacted with one single alkylene oxide or combinations of two or more different alkylene oxides. Using two or more different alkylene oxides, the resulting polymer can be obtained as a block-wise structure or a random structure.

The molar ratio of molar ratio of 1,3-diol to $C_2$-$C_{18}$ alkylene oxides at which the alkoxylation reaction is carried out lies in the range of 1:2 to 1:10, preferably in the range of 1:3 to 1:8, even more preferably in the range of 1:4 to 1:6.

This reaction is undertaken generally in the presence of a catalyst in an aqueous solution at a reaction temperature from about 70 to about 200° C. and preferably from about 80 to about 160° C. This reaction may be affected at a pressure of up to about 10 bar, and in particular up to about 8 bar.

Examples of suitable catalysts are basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. Preference is given to alkali metal hydroxides, particular preference being given to potassium hydroxide and sodium hydroxide. Typical use amounts for the base are from 0.05 to 10% by weight, in particular from 0.1 to 2% by weight, based on the total amount of polyalkyleneimine and alkylene oxide.

Alkoxylation with x+y $C_2$-$C_{18}$ alkylene oxides leads to structures as drawn in Formula IV and/or Formula V

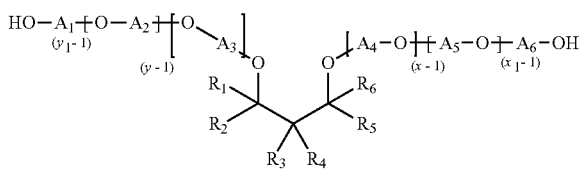

Formula (IV)

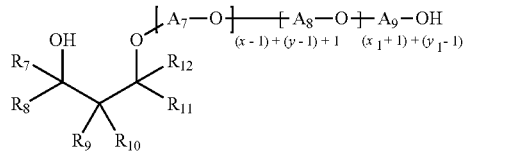

Formula (V)

wherein $R_1$-$R_{12}$ are independently selected from H, alkyl, cycloalkyl, aryl, alkylaryl, or arylalkyl,
wherein at least one of $R_1$-$R_6$ and at least one of $R_7$-$R_{12}$ is different from H,
wherein $A_1$-$A_9$ are independently selected from linear or branched alkylenes having 2 to 18 carbon atoms, preferably 2-10 carbon atoms, most preferably 2-5 carbon atoms,
and wherein the sum of x+y is in the range of about 2 to about 200, wherein x≥21 and y≥1; and $x_1+y_1$ is in the range of about 2 to about 200, preferably 2-20, most preferably 2-10, wherein $x_1$≥1 and $y_1$≥1.

Step b): Amination

Amination of the alkoxylated 1,3-diols can be carried out by two different methods, either reductive amination (b1) or reductive cyanoethylation (b2), and leads to new structures with Formula I and/or (II):

Formula (I)

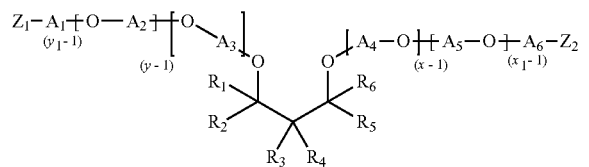

Formula (II)

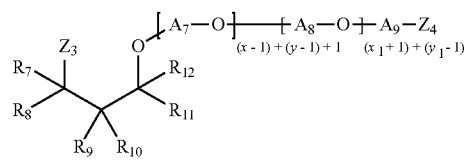

wherein $R_1$-$R_{12}$ are independently selected from H, alkyl, cycloalkyl, aryl, alkylaryl, or arylalkyl,
wherein at least one of $R_1$-$R_6$ and at least one of $R_7$-$R_{12}$ is different from H,
wherein $A_1$-$A_9$ are independently selected from linear or branched alkylenes having 2 to 18 carbon atoms, preferably 2-10 carbon atoms, most preferably 2-5 carbon atoms,
wherein $Z_1$-$Z_4$ are independently selected from OH or $CH_2CH_2CH_2NH_2$, $NH_2$, NHR' or NR'R",
wherein the degree of amination is <50%, wherein R' and R" are independently selected from alkylenes having 2 to 6 carbon atoms, and wherein the sum of x+y is in the range of about 2 to about 200, wherein x≥1 and y≥1; and $x_1+y_1$ is in the range of about 2 to about 200, preferably 2-20, most preferably 2-10, wherein $x_1$≥1 and $y_1$≥1.

Step b1 and step b2 are alternative methods to obtain molecules of Formula (I) and/or Formula (II).

Step b1): Reductive Amination

Polyetheramines according to Formula (I) and/or (II) are obtained by reductive amination of the alkoxylated 1,3-diol mixture (Formula IV and V) with ammonia in presence of hydrogen and a catalyst containing nickel. Suitable catalysts are described in WO 2011/067199 A1 and in WO2011/067200 A1, and in EP0696572 B1. Preferred catalysts are supported copper-, nickel- and cobalt-containing catalysts, wherein the catalytically active material of the catalysts, before the reduction thereof with hydrogen, comprises oxygen compounds of aluminium, of copper, of nickel and of cobalt, and in the range from 0.2 to 5.0% by weight of oxygen compounds of tin, calculated as SnO. Other preferred catalysts are supported copper-, nickel- and cobalt-containing catalysts, wherein the catalytically active material of the catalysts, before the reduction thereof with hydrogen, comprises oxygen compounds of aluminium, of copper, of nickel, of cobalt and of tin, and in the range from 0.2 to 5.0% by weight of oxygen compounds of yttrium, of lanthanum, of cerium and/or of hafnium, each calculated as $Y_2O_3$, $La_2O_3$, $Ce_2O_3$ and $Hf_2O_3$ respectively. Another preferred catalyst is a zirconium, copper, nickel catalyst, wherein the catalytically active composition comprises from 20 to 85% by weight of oxygen-containing zirconium compounds, calculated as ZrO2, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of aluminium and/or manganese, calculated as Al2O3 and MnO2 respectively.

For the reductive amination step as well supported as non-supported catalyst can be used. The supported catalyst e.g. is obtained by deposition of the metallic components of the catalyst compositions onto support materials known to those skilled in the art, using techniques which are well-known in the art including without limitation, known forms of alumina, silica, charcoal, carbon, graphite, clays, mordenites; and molecular sieves, to provide supported catalysts as well. When the catalyst is supported, the support particles of the catalyst may have any geometric shape, for example the shape of spheres, tablets or cylinders in a regular or irregular version.

The process can be carried out in a continuous or discontinuous mode, e.g. in an autoclave, tube reactor or fixed-bed reactor. The reactor design is also not narrowly critical. The feed thereto may be upflowing or downflowing, and design features in the reactor which optimize plug flow in the reactor may be employed.

Byproducts which contain secondary or tertiary amino functions may be formed under amination reaction conditions. Secondary amines are e.g. obtained from a reaction of a fully or partially aminated diol with another fully and/or partially aminated diol. Tertiary amines are formed e.g. via a reaction of a secondary amine with another fully or partially aminated diol.

Step b2): Reductive Cyanoethylation

Polyetheramines according to Formula (I) and/or (II) are obtained by reductive cyanoethylation of the alkoxylated 1,3-diol mixture (Formula IV and V). The reductive cyanoethylation is carried out by reaction of polyetheramines according to Formula (I) and/or (II) with acrylonitrile in the presence of a base followed by hydrogenation with hydrogen and a catalyst.

Bases used are typically alkaline hydroxides, and substituted ammonium hydroxide. Preferably, tetrakis(2-hydroxyethyl)ammonium hydroxide is used as a base.

As catalysts for hydrogenation the nitrile function to the corresponding amine, it is possible to use, in particular, catalysts which comprise one or more elements of the $8^{th}$ transition group of the Periodic Table (Fe, Co, Ni, Ru, Rh, Pd, Os, Ir, Pt), preferably Fe, Co, Ni, Ru or Rh, particularly preferably Co or Ni, in particular Co, as active component. A further preferred active component is Cu.

The abovementioned catalysts can be doped in the usual way with promoters, for example chromium, iron, cobalt, manganese, molybdenum, titanium, tin, metals of the alkali metal group, metals of the alkaline earth metal group and/or phosphorus.

As catalysts, preference can be given to using skeletal catalysts (also referred to as Raney® type, hereinafter also: Raney catalyst) which are obtained by leaching (activating) an alloy of hydrogenation-active metal and a further component (preferably Al). Preference is given to using Raney nickel catalysts or Raney cobalt catalysts.

Furthermore, supported Pd or Pt catalysts are preferably used as catalysts. Preferred support materials are activated carbon, Al2O3, TiO2, ZrO2 and SiO2. In a very preferred embodiment, catalysts produced by reduction of catalyst precursors are used in the process of the invention.

The catalyst precursor comprises an active composition which comprises one or more catalytically active components, optionally promoters and optionally a support material.

The catalytically active components are oxygen-comprising compounds of the above-mentioned metals, for example the metal oxides or hydroxides thereof, e.g. CoO, NiO, CuO and/or mixed oxides thereof.

For the purposes of the present patent application, the term "catalytically active components" is used for above-mentioned oxygen-comprising metal compounds but is not intended to apply that these oxygen-comprising compounds are themselves catalytically active. The catalytically active components generally display catalytic activity in the reaction according to the invention only after reduction.

Particular preference is given to catalyst precursors such as the oxide mixtures which are disclosed in EP-A-0636409 and before reduction with hydrogen comprise from 55 to 98% by weight of Co, calculated as CoO, from 0.2 to 15% by weight of phosphorus, calculated as $H_3PO_4$, from 0.2 to 15% by weight of manganese, calculated as $MnO_2$, and from 0.2 to 5.0% by weight of alkali metal, calculated as $M_2O$ (M=alkali metal), or oxide mixtures which are disclosed in EP-A-0742045 and before reduction with hydrogen comprise from 55 to 98% by weight of Co, calculated as CoO, from 0.2 to 15% by weight of phosphorus, calculated as H3PO4, from 0.2 to 15% by weight of manganese, calculated as MnO2, and from 0.05 to 5% by weight of alkali metal, calculated as M2O (M=alkali metal), or oxide mixtures which are disclosed in EP-A-696572 and before reduction with hydrogen comprise from 20 to 85% by weight of ZrO2, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$, for example the having the composition 31.5% by weight of $ZrO_2$, 50% by weight of NiO, 17% by weight of CuO and 1.5% by weight of $MoO_3$, or oxide mixtures which are disclosed in EP-A-963 975 and before reduction with hydrogen comprise from 22 to 40% by weight of ZrO2, from 1 to 30% by weight of oxygen-comprising compounds of copper, calculated as CuO, from 15 to 50% by weight of oxygen-comprising compounds of nickel, calculated as NiO, with the molar ratio of Ni:Cu being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst having the composition 33% by weight of Zr, calculated as $ZrO_2$, 28% by weight of Ni, calculated as NiO, 11% by weight of Cu, calculated as CuO, and 28% by weight of Co, calculated as CoO.

The process can be carried out in a continuous or discontinuous mode, e.g. in an autoclave, tube reactor or fixed-bed reactor. The reactor design is also not narrowly critical. The feed thereto may be upflowing or downflowing, and design features in the reactor which optimize plug flow in the reactor may be employed.

In context with the present invention, for products obtained according to the method described in step b1 and for products obtained according to the method described in step b2, the degree of amination is <50%, preferably 10 to <50%, more preferably 20 to <50%, and even more preferably 30 to <50%.

Unless specified otherwise herein, the degree of amination is calculated from the total amine value (AZ) divided by sum of the total acetylables value (AC) and tertiary amine value (tert. AZ) multiplied by 100: (Total AZ: (AC+tert. AZ)×100).

The total amine value (AZ) is determined according to DIN 16945.

The total acetylables value (AC) is determined according to DIN 53240.

The secondary and tertiary amine are determined according to ASTM D2074-07.

The hydroxyl value is calculated from (total acetylables value+tertiary amine value)−total amine value.

In another preferred embodiment, the etheramines of the invention can also be further reacted with an acid. The acid may be selected from the group consisting of citric acid, lactic acid, sulfuric acid, methanesulfonic acid, hydrogen chloride, phosphoric acid, formic acid, acetic acid, propionic acid, valeric acid, oxalic acid, succinic acid, adipic acid, sebacic acid, glutaric acid, glucaric acid, tartaric acid, malic acid, benzoic acid, salicylic acid, phthalic acid, oleic acid, stearic acid and mixtures thereof. In an alternative embodiment, the etheramines of the invention may, in protonated form, have a surfactant as a counter ion, as obtained from e.g. linear alkyl benzene sulphonic acid.

Tertiary dialkyl-substituted polyether amines can be prepared from the respective primary polyether amines by reductive amination. Typical procedures involve the use of formaldehyde or other alkylaldehydes like ethanal, 1-propanal or 1-butanal in the presence of a hydrogen donor such as formic acid or the in the presence of hydrogen gas and a transition metal containing catalyst.

Alternatively, dialky-substituted tertiary polyether amines can be obtained by reacting a polyether alcohol with a dialkylamine like e.g. dimethylamine in the presence of a suitable transition metal catalyst, preferably in the additional presence of hydrogen and under continuous removal of the reaction water.

Applications:

The inventive etheramine mixtures may be used in personal care, especially in shampoo and body wash formulations.

They may also be used as curing agent for epoxy resins or as a reactant in the production of polymers but also in polyurethanes, polyureas, epoxy resins, polyamides.

The inventive polyetheramines have proved to be effective for removal of stains, particularly grease, from soiled material. Besides, cleaning compositions with inventive polyetheramines also do not have the cleaning negatives seen with conventional, amine cleaning compositions for hydrophilic bleachable stains, such as coffee, tea, wine, or particulates. Additionally, for stain removal from white fabric, cleaning compositions with inventive polyetheramines do not cause the whiteness negatives that commercially available, amine cleaning compositions cause.

A further advantage of cleaning compositions comprising the inventive polyetheramines is their ability to remove grease stains in cold water cleaning solutions, via pretreatment of the grease stain outside the washing machine, followed by cold water washing. Without being limited by theory, cold water solutions have the effect of causing greases to harden or solidify, making greases more resistant to removal, especially from fabric. Cleaning compositions with etheramine mixtures according to Formula (I) and/or (II) however, are surprisingly effective when used in pretreatment followed by cold water cleaning.

As used herein the phrase "cleaning composition" includes compositions and formulations designed for cleaning soiled material. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, liquid hand dishwashing composition, detergent contained on or in a porous substrate or nonwoven sheet, automatic dish-washing agent, hard surface cleaner, and other suitable forms that may be apparent to one skilled in the art in view of the teachings herein. Such compositions may be used as a pre-laundering treatment, a post-laundering treatment, may be added during the rinse or wash cycle of the laundering operation, or used in homecare cleaning applications. The cleaning compositions may have a form selected from liquid, powder, single-phase or multi-phase unit dose, pouch, tablet, gel, paste, bar, or flake.

The cleaning compositions described herein may include from about 0.1% to about 10%, in some examples, from about 0.2% to about 5%, and in other examples, from about 0.5% to about 3%, by weight the composition, of an amine-terminated polyalkylene glycol of Formula I and/or II.

The inventive etheramine mixtures are effective for removal of stains, particularly grease, from soiled material. Cleaning compositions containing the amine-terminated polyalkylene glycols of the invention also do not exhibit the cleaning negatives seen with conventional amine-containing cleaning compositions on hydrophilic bleachable stains, such as coffee, tea, wine, or particulates. Additionally, unlike conventional amine-containing cleaning compositions, the amine-terminated polyalkylene glycols of the invention do not contribute to whiteness negatives on white fabrics.

A further advantage of cleaning compositions containing the inventive etheramine mixture is their ability to remove grease stains in cold water, for example, via pretreatment of a grease stain followed by cold water washing. Without being limited by theory, it is believed that cold water washing solutions have the effect of hardening or solidifying grease, making the grease more resistant to removal, especially on fabric. Cleaning compositions containing the amine-terminated polyalkylene glycols of the invention are surprisingly effective when used as part of a pretreatment regimen followed by cold water washing.

Surfactant System

The cleaning compositions comprise a surfactant system in an amount sufficient to provide desired cleaning properties. In some embodiments, the cleaning composition comprises, by weight of the composition, from about 1% to about 70% of a surfactant system. In other embodiments, the liquid cleaning composition comprises, by weight of the composition, from about 2% to about 60% of the surfactant system. In further embodiments, the cleaning composition comprises, by weight of the composition, from about 5% to about 30% of the surfactant system. The surfactant system may comprise a detersive surfactant selected from anionic surfactants, nonionic surfactants, cationic surfactants, zwitterionic surfactants, amphoteric surfactants, ampholytic surfactants, and mixtures thereof. Those of ordinary skill in the art will understand that a detersive surfactant encompasses any surfactant or mixture of surfactants that provide cleaning, stain removing, or laundering benefit to soiled material.

Adjunct Cleaning Additives

The cleaning compositions of the invention may also contain adjunct cleaning additives. Suitable adjunct cleaning additives include builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, hueing agents, dye transfer inhibiting agents, chelating agents, suds supressors, softeners, and perfumes.

METHODS OF USE

The present invention includes methods for cleaning soiled material. As will be appreciated by one skilled in the art, the cleaning compositions of the present invention are suited for use in laundry pretreatment applications, laundry cleaning applications, and home care applications. Such methods include, but are not limited to, the steps of contacting cleaning compositions in neat form or diluted in wash liquor, with at least a portion of a soiled material and then optionally rinsing the soiled material. The soiled material may be subjected to a washing step prior to the optional rinsing step.

For use in laundry pretreatment applications, the method may include contacting the cleaning compositions described herein with soiled fabric. Following pretreatment, the soiled fabric may be laundered in a washing machine or otherwise rinsed.

Machine laundry methods may comprise treating soiled laundry with an aqueous wash solution in a washing machine having dissolved or dispensed therein an effective amount of a machine laundry cleaning composition in accord with the invention. An "effective amount" of the cleaning composition means from about 20 g to about 300 g of product dissolved or dispersed in a wash solution of volume from about 5 L to about 65 L. The water temperatures may range from about 5° C. to about 100° C. The water to soiled material (e.g., fabric) ratio may be from about 1:1 to about 20:1. In the context of a fabric laundry composition, usage levels may also vary depending not only on the type and severity of the soils and stains, but also on the wash water temperature, the volume of wash water, and the type of washing machine (e.g., top-loading, front-loading, top-loading, vertical-axis Japanese-type automatic washing machine).

The cleaning compositions herein may be used for laundering of fabrics at reduced wash temperatures. These methods of laundering fabric comprise the steps of delivering a laundry cleaning composition to water to form a wash liquor and adding a laundering fabric to said wash liquor, wherein the wash liquor has a temperature of above 0° C. to about 20° C., or to about 15° C., or to about 10° C. The fabric may be contacted to the water prior to, or after, or simultaneous with, contacting the laundry cleaning composition with water.

Another method includes contacting a nonwoven substrate impregnated with an embodiment of the cleaning composition with soiled material. As used herein, "nonwoven substrate" can comprise any conventionally fashioned nonwoven sheet or web having suitable basis weight, caliper (thickness), absorbency, and strength characteristics. Non-limiting examples of suitable commercially available nonwoven substrates include those marketed under the tradenames SONTARA® by DuPont and POLYWEB® by James River Corp.

Hand washing methods, and combined handwashing with semiautomatic washing machines, are also included.

Machine Dishwashing Methods

Methods for machine-dishwashing or hand dishwashing soiled dishes, tableware, silverware, or other kitchenware, are included. One method for machine dishwashing comprises treating soiled dishes, tableware, silverware, or other kitchenware with an aqueous liquid having dissolved or dispensed therein an effective amount of a machine dishwashing composition in accord with the invention. By an effective amount of the machine dishwashing composition it is meant from about 8 g to about 60 g of product dissolved or dispersed in a wash solution of volume from about 3 L to about 10 L.

One method for hand dishwashing comprises dissolution of the cleaning composition into a receptacle containing water, followed by contacting soiled dishes, tableware, silverware, or other kitchenware with the dishwashing liquor, then hand scrubbing, wiping, or rinsing the soiled dishes, tableware, silverware, or other kitchenware. Another method for hand dishwashing comprises direct application of the cleaning composition onto soiled dishes, tableware, silverware, or other kitchenware, then hand scrubbing, wiping, or rinsing the soiled dishes, tableware, silverware, or other kitchenware. In some examples, an effective amount of cleaning composition for hand dishwashing is from about 0.5 ml. to about 20 ml. diluted in water.

Packaging for the Compositions

The cleaning compositions described herein can be packaged in any suitable container including those constructed from paper, cardboard, plastic materials, and any suitable laminates. An optional packaging type is described in European Application No. 94921505.7.

Multi-Compartment Pouch Additive

The cleaning compositions described herein may also be packaged as a multi-compartment cleaning composition.

EXAMPLES

Example 1a: 1 Mol 2-Butyl-2-Ethyl-1,3-Propanediol+5.6 Mole Propylene Oxide

In a 2 l autoclave 313.1 g 2-Butyl-2-ethyl-1,3-propane diol and 3.8 g KOH (50% in water) were mixed and stirred under vacuum (<10 mbar) at 120° C. for 2 h. The autoclave was purged with nitrogen and heated to 140° C. 635.6 g propylene oxide was added in portions within 6 h. To complete the reaction, the mixture was allowed to post-react for additional 5 h at 140° C. The reaction mixture was stripped with nitrogen and volatile compounds were removed in vacuo at 80° C. The catalyst was removed by adding 50.9 g water and 8.2 g phosphoric acid (40% in water) stirring at 100° C. for 0.5 h and dewatering in vacuo for 2 hours. After filtration 930.0 g of a light yellowish oil was obtained (hydroxy value: 233 mgKOH/g).

Example 1b: 1 Mol 2-Butyl-2-Ethyl-1,3-Propanediol+5.6 Mole Propylene Oxide, Partially Aminated (32% Amination Degree)

The amination of (1a) was conducted in a tubular reactor (length 500 mm, diameter 18 mm) which had been charged with 15 mL of silica (3×3 mm pellets) followed by 70 mL (74 g) of the catalyst precursor (containing oxides of nickel, cobalt, copper and tin on gamma-$Al_2O_3$, 1.0-1.6 mm split—prepared according to WO 2013/072289 A1) and filled up with silica (ca. 15 mL).

The catalyst was activated at atmospheric pressure by being heated to 100° C. with 25 Nl/h of nitrogen, then 3 hours at 150° C. in which the hydrogen feed was increased from 2 to 25 Nl/h, then heated to 280° C. at a heating rate of 60° C. per hour and kept at 280° C. for 12 hours. The reactor was cooled to 100° C., the nitrogen flow was turned off and the pressure was increased to 120 bar.

The catalyst was flushed with ammonia at 100° C., before the temperature was increased to 175° C. and the alcohol feed was started with a WHSV of 0.44 kg/liter*h (molar ratio ammonia/alcohol=27:1, hydrogen/alcohol=6:1). The crude material was collected and stripped on a rotary evaporator to remove excess ammonia, light weight amines and reaction water to afford the aminated material. The analytical data of the reaction product is shown in Table 1.

TABLE 1

| Properties of reaction product of Example 1b. | | | | | | |
|---|---|---|---|---|---|---|
| Total amine-value mg KOH/g | Total acetylatables mg KOH/g | Secondary and tertiary amine value mg KOH/g | Tertiary amine-value mg KOH/g | Hydroxyl value mg KOH/g | Grade of amination in % | Primary Amine in % of total amine |
| 75.87 | 237.00 | 0.16 | 0.00 | 161.13 | 32.01 | 99.79 |

Use as Additives in Laundry Detergents

Technical stain swatches of blue knitted cotton containing Beef Fat, Pork Fat, Sausage Fat, Chicken Fat and Bacon Grease were purchased from Warwick Equest Ltd. and washed in conventional western European washing machines (Miele Waschmaschine Softronic W 2241), selecting a 59 min washing cycle without heating and using 75 g of liquid detergent composition LA1 (table 9) together with or without 1.125 g of polyetheramine additive and some hydrochloric acid to readjust the pH after addition of the polyetheramine. (pH of 75 g of LA1 (Tab. 2) in 1 L water should be at pH=8.3.) Water hardness was 2.5 mM ($Ca^{2+}$: $Mg^{2+}$ was 3:1). Standard colorimetric measurement was used to obtain L*, a* and b* values for each stain before and after the washing. From L*, a* and b* values the stain level was calculated.

Stain removal from the swatches was calculated as follows:

$$\text{Stain Removal Index } (SRI) = \frac{(\Delta E_{initial} - \Delta E_{washed})}{\Delta E_{initial}} \times 100$$

$\Delta E_{initial}$ = Stain level before washing

-continued $\Delta E_{washed}$ = Stain level after washing $\Delta E$ is calculated as CIE 1976 color difference according to DIN EN ISO 11664-4 (June 2012). $\Delta E_{initial}$ is calculated with L*, a*, b* values measured on fabric without stain and the L*, a*, b* values measured on the greasy stain before washing. $\Delta E_{washed}$ is calculated with L*, a*, b* values measured on fabric without stain and the L*, a*, b* values measured on the greasy stain after washing. Standard colorimetric measurement was used to obtain L*, a* and b* values.

Four replicates for each stain type have been carried out. Given below are the averaged values. Stain level corresponds to the amount of grease on the fabric. The stain level of the fabric before the washing ($\Delta E_{initial}$) is high, in the washing process stains are removed and the stain level after washing is smaller ($\Delta E_{washed}$). The better the stains have been removed the lower the value for $\Delta E_{washed}$ will be and the higher the difference will be to $\Delta E_{initial}$. Therefore the value of stain removal index increases with better washing performance.

TABLE 2

| liquid detergent composition LA1 | |
| --- | --- |
| Ingredients of liquid detergent composition LA1 | percentage by weight |
| Alkyl Benzene sulfonate[1] | 7.50% |
| AE3S[2] | 2.60% |
| AE9[3] | 0.40% |
| NI 45-7[4] | 4.40% |
| Citric Acid | 3.20% |
| C1218 Fatty acid | 3.10% |
| Amphiphilic polymer[5] | 0.50% |
| Zwitterionic dispersant[6] | 1.00% |
| Ethoxylated Polyethyleneimine[7] | 1.51% |
| Protease[8] | 0.89% |
| Enymes[9] | 0.21% |
| Chelant[10] | 0.28% |
| Brightener[11] | 0.09% |
| Solvent | 7.35% |
| Sodium Hydroxide | 3.70% |
| Fragrance & Dyes | 1.54% |
| Water, filler, stucturant | To Balance |

[1]Linear alkylbenenesulfonate having an average aliphatic carbon chain length C11-C12 supplied by Stepan, Northfield Illinois, USA
[2]AE3S is C12-15 alkyl ethoxy (3) sulfate supplied by Stepan, Northfield, Illinois,USA
[3]AE9 is C12-14 alcohol ethoxylate, with an average degree of ethoxylation of 9, supplied by Huntsman, Salt Lake City, Utah, USA
[4]NI 45-7 is C14-15 alcohol ethoxylate, with an average degree of ethoxylation of 7, supplied by Huntsman, Salt Lake City, Utah, USA
[5]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[6]A compound having the following general structure: bis((C2H5O)(C2H4O)n)(CH3)—N+—CxH2x—N+—(CH3)-bis((C2H5O)(C2H4O)n), wherein n = from 20 to 30, and x = from 3 to 8, or sulphated or sulphonated variants thereof
[7]Polyethyleneimine (MW = 600) with 20 ethoxylate groups per—NH
[8]Proteases may be supplied by Genencor International, Palo Alto, California, USA (e.g. Purafect Prime ®) or by Novozymes, Bagsvaerd, Denmark (e.g. Liquanase ®, Coronase ®).
[9]Natalase ®, Mannaway ® are all products of Novozymes, Bagsvaerd, Denmark.
[10]Suitable chelants are, for example, diethylenetetraamine pentaacetic acid (DTPA) supplied by Dow Chemical, Midland, Michigan, USA or Hydroxyethane di phosphonate (HEDP) or diethylene triamine penta(methyl phosphonic) acid supplied by Solutia, St Louis, Missouri, USA;
[11]Fluorescent Brightener 1 is Tinopal ® AMS, Fluorescent Brightener 2 supplied by Ciba Specialty Chemicals, Basel, Switzerland

| Washing Test 1: Initial water temperature at 22° C. | | |
| --- | --- | --- |
| Stain | SRI for A | SRI for B |
| Beef Fat | 72.9 | 78.0 |
| Pork Fat | 68.8 | 73.8 |
| Bacon Grease | 68.6 | 72.9 |

A: liquid detergent composition LA1 (see Table 2) without additional etheramine additive
B: liquid detergent composition LA1 (see Table 2) with (1 mol 2-butyl-2-ethyl-1,3-propanediol + 5.6 mole propylene oxide, partially aminated (32% amination degree)) as described in example 1b.

The invention claimed is:

1. An etheramine mixture comprising at least 90% by weight, based on the total weight of the etheramine mixture, of an etheramine of at least one of Formula (I) and an etheramine of at least one of Formula (II), Formula (I)
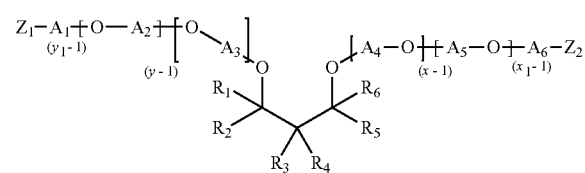

Formula (II)
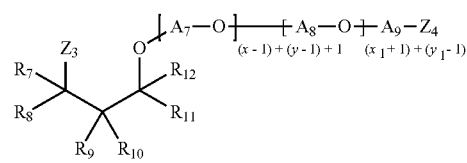

wherein R1-R12 are independently selected from H, alkyl, cycloalkyl, aryl, alkylaryl, or arylalkyl, wherein at least one of R1-R6 and at least one of R7-R12 is different from H,
wherein A1-A9 are independently selected from one of linear or branched alkylenes having 2 to 18 carbon atoms, wherein Z1-Z4 are independently selected from OH, CH2CH2CH2NH2, NH2, NHR' or NR'R", wherein the degree of amination is <50%,
wherein R' and R" are independently selected from alkylenes having 2 to 6 carbon atoms, and wherein the sum of x+y is in the range of from 2 to 200, wherein x≥1 and y≥1; and
x1+y1 is in the range of from 2 to 200.

2. The etheramine mixture according to claim 1, wherein the etheramine mixture comprises at least 95% by weight, based on the total weight of the etheramine mixture, of the etheramine of Formula (I) and the etheramine of Formula (II).

3. The etheramine mixture according to claim 1, wherein in said etheramine of Formula (I) or Formula (II), x+y is in the range of from 2 to 20.

4. The etheramine mixture according to claim 1, wherein in said etheramine of Formula (I) or Formula (II), x+y is in the range of from 3 to 20.

5. The etheramine mixture according to claim 1, wherein in said etheramine of Formula (I) or Formula (II), the degree of amination lies in the range of 30% to <50%.

6. The etheramine mixture according to claim 1, wherein in said etheramine of Formula (I) or Formula (II), A1-A9 are independently selected from the group consisting of ethylene, propylene, and butylene.

7. The etheramine mixture according to claim 1, wherein in said etheramine of Formula (I) or Formula (II), each of A1-A9 is propylene.

8. The etheramine mixture according to claim 1, wherein in said etheramine of Formula (I) or Formula (II), R1, R2, R5, R6, R7, R8, R11, and R12 are H and R3, R4, R9, and R10 are independently selected from C1-16 alkyl or aryl.

9. The etheramine mixture according to claim 1, wherein in said etheramine of Formula (I) or Formula (II), R1, R2, R5, R6, R7, R8, R11, and R12 are H and R3, R4, R9, and R10 are independently selected from a butyl group, an ethyl group, a methyl group, a propyl group, or a phenyl group.

10. The etheramine mixture according to claim 1, wherein in said etheramine Formula (I) or Formula (II), R3 and R9 are each an ethyl group, R1, R2, R5 R6, R7, R8, R11, R12 are each H, R4 and R10 are each a butyl group.

11. The etheramine mixture according to claim 1, wherein the etheramine of each of Formula (I) and Formula (II) has a weight average molecular weight of about 290 to about 1000 grams/mole.

12. The etheramine mixture according to claim 1, wherein the etheramine of each of Formula (I) and Formula (II) is reacted with an acid.

13. A process for the manufacture of an etheramine mixture comprising at least 90% by weight, based on the total weight of the etheramine mixture, of an etheramine of at least one of Formula (I) and an etheramine of at least one of Formula (II) according to claim 1 comprising the following steps:
    a) reacting a 1,3-diol of Formula (III) with C2-C18 alkylene oxides, wherein the molar ratio of 1,3-diol to C2-C18 alkylene oxides is in the range of 1:2 to 1:10,

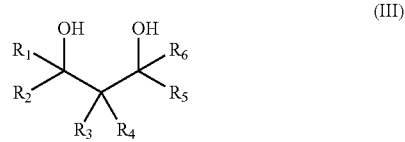

(III)

wherein R1-R6 are independently of one another H, alkyl, cycloalkyl, aryl, alkylaryl, or arylalkyl and at least one group selected from R1-R6 is different from H, followed by one of:

b1) aminating the alkoxylated 1, 3-diols with ammonia, and
    b2) reductive cyanoethylation of the alkoxylated 1, 3-diols.

14. The process according to claim 13, wherein the molar ratio of 1,3-diol to C2-C18 alkylene oxides is in the range of 1:3 to 1:8.

15. The process according to claim 13, wherein the molar ratio of 1,3-diol to C2-C18 alkylene oxides is in the range of 1:4 to 1:6.

16. The process according to claim 13, wherein the C2-C18 alkylene oxides are selected from the group consisting of ethylene oxide, propylene oxide, butylene oxide and a mixture thereof.

17. The process according to claim 13, wherein the C2-C18 alkylene oxide is propylene oxide.

18. The process according to claim 13, wherein the 1,3-diol of formula (III) is selected from the group consisting of 2-butyl-2-ethyl-1,3-propanediol, 2-methyl-2-propyl-1,3-propanediol, 2-methyl-2-phenyl-1,3-propanediol, 2,2-dimethyl-1,3-propandiol, and 2-ethyl-1,3-hexandiol.

19. The process according to claim 13, wherein the amination is carried out in the presence of copper-, nickel- or cobalt-containing catalyst.

20. The process according to claim 19, wherein the catalytically active material of the catalysts, before the reduction thereof with hydrogen, comprises oxygen compounds of aluminum, of copper, of nickel and of cobalt, and in the range from 0.2 to 5.0% by weight of oxygen compounds of tin, calculated as SnO.

21. A composition for use in at least one of personal care, shampoo, and body wash formulations, the composition comprising the etheramine mixture of claim 1.

22. A composition for use as a curing agent, the composition comprising the etheramine mixture of claim 1.

23. A composition for use as a reactant in the production of polymers, the composition comprising the etheramine mixture of claim 1.

24. A composition for use in at least one of polyurethanes, polyureas, and thermoplastic polyamide adhesives, the composition comprising the etheramine mixture of claim 1.

\* \* \* \* \*